US011423540B2

(12) United States Patent
Heindl et al.

(10) Patent No.: US 11,423,540 B2
(45) Date of Patent: Aug. 23, 2022

(54) SEGMENTATION OF ANATOMICAL REGIONS AND LESIONS

(71) Applicant: KHEIRON MEDICAL TECHNOLOGIES LTD, London (GB)

(72) Inventors: Andreas Heindl, London (GB); Galvin Khara, London (GB); Joseph Yearsley, London (GB); Michael O'Neill, London (GB); Peter Kecskemethy, London (GB); Tobias Rijken, London (GB)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 15 days.

(21) Appl. No.: 16/604,660

(22) PCT Filed: Apr. 12, 2018

(86) PCT No.: PCT/GB2018/050980
§ 371 (c)(1),
(2) Date: Oct. 11, 2019

(87) PCT Pub. No.: WO2018/189550
PCT Pub. Date: Oct. 18, 2018

(65) Prior Publication Data
US 2020/0167928 A1 May 28, 2020

(30) Foreign Application Priority Data

Apr. 12, 2017 (GB) .................................. 1705911
Jul. 18, 2017 (GB) .................................. 1711558
Jul. 18, 2017 (GB) .................................. 1711560

(51) Int. Cl.
*G06K 9/00* (2022.01)
*G06T 7/00* (2017.01)
(Continued)

(52) U.S. Cl.
CPC ............ *G06T 7/0014* (2013.01); *A61B 5/055* (2013.01); *A61B 5/4312* (2013.01);
(Continued)

(58) Field of Classification Search
CPC ..................................................... G06T 7/0014
See application file for complete search history.

(56) References Cited

U.S. PATENT DOCUMENTS 6,075,879 A    6/2000  Roehrig et al.
6,324,532 B1 * 11/2001  Spence .................. G06V 10/82
                                                                706/19
(Continued)

FOREIGN PATENT DOCUMENTS

CN          105931226 A      9/2016
CN          106096491 A     11/2016
(Continued)

OTHER PUBLICATIONS

Kallenberg et al (NPL "Unsupervised Deep Learning Applied to Mammographic Risk Scoring", IEEE Transactions on Medical Imaging, vol. 35, No. 5, May 2016, hereafter referred to as Kallenberg).*
(Continued)

*Primary Examiner* — Oneal R Mistry
(74) *Attorney, Agent, or Firm* — Finch & Maloney PLLC

(57) ABSTRACT

The present invention relates to deep learning for automated segmentation of a medical image. More particularly, the present invention relates to deep learning for automated segmentation of anatomical regions and lesions in mammography screening and clinical assessment.

According to a first aspect, there is provided a computer-aided method of segmenting regions in medical images, the method comprising the steps of: receiving input data; analysing the input data by identifying one or more regions;
(Continued)

determining one or more characteristics for the one or more regions in the input data; and generating output segmentation data in dependence upon the characteristics for the one or more regions.

20 Claims, 4 Drawing Sheets

(51) Int. Cl.
| | |
|---|---|
| G06T 7/11 | (2017.01) |
| G16H 30/20 | (2018.01) |
| G16H 50/20 | (2018.01) |
| G16H 30/40 | (2018.01) |
| A61B 5/00 | (2006.01) |
| A61B 6/00 | (2006.01) |
| G06N 3/08 | (2006.01) |
| G06T 7/143 | (2017.01) |
| A61B 5/055 | (2006.01) |
| A61B 6/03 | (2006.01) |
| G06T 7/136 | (2017.01) |
| G06T 7/33 | (2017.01) |
| G16H 50/30 | (2018.01) |

(52) U.S. Cl.
CPC .......... *A61B 5/7264* (2013.01); *A61B 5/7267* (2013.01); *A61B 5/7282* (2013.01); *A61B 6/032* (2013.01); *A61B 6/502* (2013.01); *A61B 6/5217* (2013.01); *G06N 3/08* (2013.01); *G06T 7/0012* (2013.01); *G06T 7/0016* (2013.01); *G06T 7/11* (2017.01); *G06T 7/136* (2017.01); *G06T 7/143* (2017.01); *G06T 7/337* (2017.01); *G16H 30/20* (2018.01); *G16H 30/40* (2018.01); *G16H 50/20* (2018.01); *G16H 50/30* (2018.01); *G06T 2207/10081* (2013.01); *G06T 2207/10088* (2013.01); *G06T 2207/10116* (2013.01); *G06T 2207/20081* (2013.01); *G06T 2207/20084* (2013.01); *G06T 2207/30068* (2013.01); *G06T 2207/30096* (2013.01)

(56) References Cited

U.S. PATENT DOCUMENTS

| | | | | |
|---|---|---|---|---|
| 6,463,425 | B2* | 10/2002 | Raz | G01N 15/1475 |
| | | | | 382/128 |
| 9,589,374 | B1* | 3/2017 | Gao | A61B 6/5211 |
| 10,127,659 | B2* | 11/2018 | Hsieh | G06N 3/08 |
| 11,127,137 | B2 | 9/2021 | Heindl et al. | |
| 2005/0113651 | A1 | 5/2005 | Wood et al. | |
| 2006/0050958 | A1 | 3/2006 | Okada et al. | |
| 2006/0274928 | A1 | 12/2006 | Collins et al. | |
| 2007/0003119 | A1 | 1/2007 | Roehrig et al. | |
| 2011/0123087 | A1 | 5/2011 | Nie et al. | |
| 2011/0150313 | A1 | 6/2011 | Su et al. | |
| 2013/0343626 | A1 | 12/2013 | Rico et al. | |
| 2014/0355840 | A1 | 12/2014 | Peyton | |
| 2016/0350946 | A1 | 12/2016 | Schieke et al. | |
| 2017/0039412 | A1 | 2/2017 | Solanki et al. | |
| 2018/0061054 | A1* | 3/2018 | Abraham | G06T 7/337 |
| 2018/0129900 | A1* | 5/2018 | Kiraly | G06K 9/6277 |
| 2018/0165809 | A1 | 6/2018 | Stanitsas et al. | |
| 2018/0218495 | A1* | 8/2018 | Ben-Ari | G06K 9/627 |
| 2018/0218497 | A1* | 8/2018 | Golden | G06N 3/0454 |
| 2020/0074632 | A1 | 3/2020 | Heindl et al. | |
| 2020/0074634 | A1 | 3/2020 | Kecskemethy et al. | |
| 2020/0342589 | A1 | 10/2020 | Heindl et al. | |

FOREIGN PATENT DOCUMENTS

| | | |
|---|---|---|
| CN | 106204587 A | 12/2016 |
| JP | 2006255412 A | 9/2006 |
| JP | 2008541889 A | 11/2008 |
| JP | 2016534709 A | 11/2016 |
| WO | 2008050332 A2 | 5/2008 |
| WO | 2008088478 A1 | 7/2008 |
| WO | 2015031641 A1 | 3/2015 |
| WO | 2015077076 A1 | 5/2015 |
| WO | 2017210690 A1 | 12/2017 |
| WO | 2018189541 A1 | 10/2018 |
| WO | 2018189549 A1 | 10/2018 |
| WO | 2018189550 A1 | 10/2018 |
| WO | 2018189551 A1 | 10/2018 |

OTHER PUBLICATIONS

International Search Report and Written Opinion received for Patent Application No. PCT/GB2018/050969, dated Jun. 26, 2018. 20 pages.
International Preliminary Report on Patentability received for Patent Application No. PCT/GB2018/050969, dated Oct. 15, 2019. 12 pages.
International Search Report and Written Opinion received for PCT Application No. PCT/GB2018/050980, dated Jul. 12, 2018. 34 pages.
International Preliminary Report on Patentability received for PCT Application No. PCT/GB2018/050980, dated Oct. 15, 2019. 11 pages.
Combined Search and Examination Report under Sections 17 and 18(3) received for GB Application No. 1711558.5, dated Dec. 22, 2017. 6 pages.
International Search Report and Written Opinion received for Patent Application No. PCT/GB2018/050979, dated Jul. 9, 2018. 36 pages.
International Preliminary Report on Patentability received for Patent Application No. PCT/GB2018/050979, dated Oct. 15, 2019. 11 pages.
Combined Search and Examination Report under Sections 17 and 18(3) received for GB Application No. 1711557.7, dated Jan. 18, 2018. 5 pages.
International Search Report and Written Opinion received for Patent Application No. PCT/GB2018/050981, dated Jul. 9, 2018. 23 pages.
International Preliminary Report on Patentability received for Patent Application No. PCT/GB2018/050981, dated Oct. 15, 2019. 15 pages.
Combined Search and Examination Report under Sections 17 and 18(3) received for GB Application No. 1711559.3 dated Dec. 19, 2017. 7 pages.
Christ, et al., "Automatic Liver and Tumor Segmentation of CT and MRI Volumes Using Cascaded Fully Convolutional Neural Networks," arXiv: 1702.05970v2 [cs.CV], Feb. 23, 2017. 20 pages.
Christ, et al., "Survivalnet: Predicting Patient Survival From Diffusion Weighted Magnetic Resonance Images Using Cascaded Fully Convolutional and 3D Convolutional Neural Networks," arXiv: 1702.05941v1 [cs.CV], Feb. 20, 2017. 6 pages.
Hou, et al., "Patch-based Convolutional Neural Network for Whole Slide Tissue Image Classification," IEEE Conference On Computer Vision and Pattern Recognition, (CVPR) Jun. 27, 2016. pp. 2424-2433.
Menechelli, et al., "Automatic breast tissue density estimation scheme in digital mammography images," Progress in Biomedical Optics and Imaging, SPIE—International Society for Optical Engineering., vol. 10136, Mar. 10, 2017. 12 pages.
Ronneberger, et al., "U-Net: Convolutional Networks for Biomedical Image Segmentation," Medical Image Computing and Computer-Assisted Intervention—MICCAI 2015—18th International Conference. Nov. 18, 2015, Springer International Publishing, arXiv: 1505.04597v1, May 18, 2015. 8 pages.
Yu, et al., "Automated Melanoma Recognition in Dermoscopy Images via Very Deep Residual Networks," IEEE Transactions On Medical Imaging. Dec. 2016. 12 pages.

(56) References Cited

OTHER PUBLICATIONS

El Hamdi, et al., "Breast Cancer Diagnosis Using a Hybrid Evolutionary Neural Network Classifier," 18th Mediterranean Conference on Control & Automation, Jun. 23-25, 2010, pp. 1308-1315.

Kallenberg, et al., "Unsupervised Deep Learning Applied to Breast Density Segmentation and Mammographic Risk Scoring," IEEE Transactions on Medical Imaging, vol. 35, No. 5, May 2016. pp. 1322-1331.

Winkel, et al., "Mammographic density and structural features can individually and jointly contribute to breast cancer risk assessment in mammography screening: a case-control study," BMC Cancer (2016) DOI 10.1186/s12885-016-2450-7. pp. 1-12.

Communication pursuant to Article 94(3) EPC received for EP Application No. 18719271.1, dated Jun. 21, 2021. 10 pages.

Communication pursuant to Article 94(3) EPC received for EP Application No. 18719272.9, dated Jun. 21, 2021. 8 pages.

Akselrod-Ballin, et al., "A Region Based Convolutional Network for Tumor Detection and Classification in Breast Mammography," Springer International Publishing AG, 2016, G. Carneiro et al. (Eds): Labels 2016/DLMIA 2016, LNCS 10008, pp. 197-205.

Gram, et al., "The Tabar classification of mammographic parenchymal patterns," ELSEVIER, European Journal of Radiology 24 (1997), pp. 131-136.

Communication pursuant to Article 94(3) EPC received for EP Application No. 18719273.7, dated Nov. 11, 2021. 9 pages.

Sun, et al., "Enhancing deep convolutional neural network scheme for breast cancer diagnosis with unlabeled data," ELSEVIER—Computerized Medical Imaging and Graphics 57 (2017). 6 pages.

Long, et al., "Fully Convolutional Networks for Semantic Segmentation," Proc. of IEEE Computer Vision and Pattern Recognition, 201, 3431-3440, https://openaccess.thecvf.com/content_cvpr_2015/papers/Long_Fully_Convolutional_Networks_2015_CVPR_paper.pdf.

JP Office Action issued for JP2020-505539, dated Mar. 8, 2022, 5 pages. (including English translation).

JP Office Action received for JP Application No. 2020-505540, dated Apr. 19, 2022. 3 pages.

* cited by examiner

SEGMENTATION OF ANATOMICAL REGIONS AND LESIONS

FIELD

The present invention relates to deep learning for automated segmentation of a medical image. More particularly, the present invention relates to deep learning for automated segmentation of anatomical regions and lesions in mammography screening and clinical assessment.

BACKGROUND

Mammography is an advancing method of scanning human breast tissue which makes use of low dose X-rays to produce detailed images of the internal structure of the human breast. The screening of these images, called mammograms, aids early detection and diagnoses of breast abnormalities and diseases. However, screening mammograms are prone to false-positive and false-negative results which may cause unwanted psychological and physiological effects.

Image segmentation, the process of partitioning an image into meaningful segments easier to analyse, is a critical step for improved image analysis and determining diagnosis and therapeutic preparation. This procedure is often challenging, and may cause difficulty when it comes to accurately and precisely detecting abnormalities or diseases.

Assessment by human manpower (for example radiologists), believed to be the most accurate method of image evaluation, refers to the task of physically "segmenting" and categorising an image spot-by-spot for comprehensive analysis. This is generally carried out by radiologists, who are highly trained in this specific type of image investigation. Image analysis is applied intensively as a post processing method, despite disadvantages such as time consumption and tendency of error.

SUMMARY OF INVENTION

Aspects and/or embodiments seek to provide a method, apparatus, and system for automated segmentation of a medical image through the use of deep learning.

According to a first aspect, there is provided a computer-aided method of segmenting regions in medical images, the method comprising the steps of: receiving input data; analysing the input data by identifying one or more regions; determining one or more characteristics for the one or more regions in the input data; and generating output segmentation data in dependence upon the characteristics for the one or more regions.

Conventional segmentation methods for identifying regions rely on an expert, usually a radiologist, providing a seed region or starting point. Often, the radiologist will segment the entire image without any computerised input, which can lead to errors owing to mistakes, carelessness, human error, and/or details too fine for the human eye to detect. Conversely, the method disclosed herein is operable to segment a region without any prior input other than an image and requires no feature engineering steps.

Such a method can be used to identify and/or segment anatomical regions and/or lesions.

Typically, anatomical regions identified through the use of this method may comprise the pectoral muscle, the parenchyma, skins folds, lymph nodes, and/or the mammilla.

Lesions, which may comprise one or more cancerous growths, masses, abscesses, lacerations, calcifications, and/or other irregularities within biological tissue, can cause serious medical problems if left undetected. Such lesions are often conventionally detected and/or analysed through a medical scan of a patient, which generates one or more medical images such as a mammogram. Therefore, it is advantageous if such lesions are operable to be segmented, and hence reviewed with greater accuracy by a medical professional.

The term segmentation does not merely represent dividing an image into one or more parts, for example, by using a bounding box around a particular region or identifying a central location of a particular region. Instead, the segmentation provided by this method determines a number of useful characteristic data, such as area, shape and size, which is more precise than traditional methods. As a result, this segmentation method can be used to more accurately indicate a malignant tumour.

Optionally, the analysis of the input data is performed using one or more Fully Convolutional Networks (FCNs). Optionally, the or each FCN comprises one or more convolutional layers. Optionally, the or each FCN comprises one or more hidden representations. Optionally, the or each FCN comprises one or more activation layers, the one or more activation layers comprising one or more rectified linear units (ReLU) and/or exponential linear units (ELU). Optionally, the or each FCN comprises one or more sigmoid activation layers and/or softmax functions for the or each region.

Convolutional networks are powerful tools inspired by biological neural processes, which can be trained to yield hierarchies of features and are particularly suited to image recognition. Convolutional layers apply a convolutional operation to an input, and pass the results to a following layer. With training, FCNs can achieve expert-level accuracy or greater with regard to segmenting and localising anatomical and pathological regions in digital medical images such as mammograms.

Optionally, the input data comprises medical image data. Optionally, the medical image data comprises one or more mammograms. Optionally, the input data comprises one or more Digital Imaging and Communications in Medicine (DICOM) files.

FCNs can also analyse medical images far more quickly than a human expert, and hence increase the number of medical images analysed overall. Therefore a problem, for example the growth of a cancerous tumour, can be detected more quickly than waiting for a human expert to become available and hence treatment may begin earlier. The identification of regions of interest, which may include lesions, may therefore aid screening and clinical assessment of breast cancer among other medical issues. Earlier diagnosis and treatment can reduce psychological stress to a patient and also increase the chances of survival in the long term.

Optionally, the medical image data comprises a 4D tensor. Optionally, the 4D tensor is of size [1, height, width, 1]. Optionally, the pixel values of the medical image data are fit to a windowing level supplied by the DICOM file and then represented as 16-bit. Optionally, the medical image data is rescaled to a width of between 750 and 900 pixels and/or a height of between 750 and 900 pixels.

The windowing level defines the range of bit values considered in the image. Medical images are conventionally 16-bit images, wherein each pixel is represented as a 16-bit integer ranging from 0 to $2^{16}-1$, i.e. [0, 1, 2, ..., 65535]. The information content is very high in these images, and generally comprises more information than what the human eye is capable of detecting. If such a medical image is analysed by a trained professional, for example a radiologist, a windowing level is typically set to limit the range of pixel values observed.

The rescaling step may be included owing to conventional hardware constraints. Medical images are typically in the region of ~3500×2500 pixels. An FCN 100 applied to this image does not fit in conventional graphics processing unit (GPU) memory. The image can be rescaled to a larger or smaller size, or even not rescaled at all, and would allow the FCN to see a higher resolution and may pick up finer detail. However this is unlikely to fit in GPU memory, and could cause both the training and identification processes to become considerably slower. By rescaling the image to a smaller size, it is more likely to be able to fit in a GPU memory, and allow both the training and identification processes to run at a faster speed. The FCN may also generalise better owing to a smaller number of input parameters. However, the effectiveness and/or accuracy of the segmentation of different regions may be reduced owing to the lower resolution. Therefore, it was concluded for this embodiment that 800×800 pixels is the optimum size image, in order to be able to fit in GPU memory with the models used. Smaller models had a negative effect on prediction performance.

Optionally, the output data comprises an overlay. Optionally, the overlay comprises a segmentation outline and/or probability map showing one or more locations of one or more regions.

Providing a clear and accurate segmentation of regions can be very helpful when reviewing a medical image, for example a mammogram. This may be especially relevant if there is reason to suspect there is a medical issue with a patient, for example a swollen area which is larger than it was in previous scans. Such changes may be more easily detectable if the different regions are clearly segmented. In addition, the segmentation information can also be used to enrich the Picture Archiving Communication Systems (PACS) that radiology departments use in hospitals. With the inclusion of this segmentation data on PACS, it advantageously improves future methods of flagging up similar cases, whether the methods are semi-automated, entirely automated or performed manually.

Optionally, voids within the segmentation outline are operable to be removed. Optionally, one or more probability masks are generated for the one or more regions. Optionally, one or more of the one or more probability masks are converted to one or more binary masks. Optionally, the conversion of the one or more of the one or more probability masks to one or more binary masks is performed by thresholding the probabilities. Optionally, one or more parts of the one or more binary masks are removed with reference to an assigned threshold.

Optionally, the segmented region comprises an anatomical region or a lesion.

If an anatomical region, for example pectoral muscle, or a lesion is detected and segmented, it is possible that a region within that segmentation is incorrectly identified or not identified at all. Therefore there may be a void within the pectoral muscle segmentation, or a different segmented region which is too small to have been correctly identified as measured against a predetermined threshold. In order to correct this error that part of the segmentation may be removed. For ease of further downstream analysis, the one or more probability masks may be in the form of one or more probability maps. The one or more binary masks may be in the form of one or more overlays as described herein. The one or more binary masks may further comprise one or more quantized masks. The or any assigned threshold referred to herein may be established through trial and error, expert advice, and/or a tuning process performed before, during, and/or the training process.

Optionally, the one or more binary masks are upscaled to the original size of the input data. Optionally, the one or more binary masks are stored in the form of a DICOM file. Optionally, the one or more binary masks comprise one or more identifications of masses and/or calcifications. Optionally, the anatomical regions comprise at least part of a human breast area.

As a DICOM file is conventionally used to store and share medical images, conforming to such a standard allows for easier distribution and future analysis of the medical images and/or any overlays or other contributory data. The one or more binary masks may be stored as part of a DICOM image file, added to an image file, and/or otherwise stored and/or represented according to the DICOM standard or portion of the standard.

Optionally, the step of analysing the input data comprises any combination of the input data comprising one or more patches; analysing the input data through sliding windows; predicting a location of one or more segmented regions in each patch; calculating a prediction score for the or each patches; and determining an overall prediction score comprising a mean score across the one or more patches.

By applying a mean calculation across a plurality of patches, the number of errors and/or inaccuracies may be reduced. An incorrect calculation for one pixel in an overlapping area may be at least partially mitigated by a correct calculation once the overlapping area is analysed again.

According to a further aspect, there is provided a computer-aided method of segmenting lesions, the method comprising the steps of: receiving input data; analysing the input data; detecting and identifying the presence of any lesions in the input data; and generating output data comprising the locations of the or each lesion if detected.

According to a further aspect, there is provided an apparatus operable to perform the method disclosed herein. According to a further aspect, there is provided a system operable to perform the method disclosed herein.

Such an apparatus and/or system may be installed in or near hospitals, or connected to hospitals via a digital network, to reduce waiting times for medical images to be analysed. Patients may therefore be spared stress from not knowing the results of a medical scan, and may receive treatment more quickly if required. The apparatus and/or system and/or method disclosed herein may further form a constituent part of a different arrangement, for example detecting and/or segmenting different objects, environments, surroundings, and/or images.

According to a further aspect, there is provided a computer program product operable to perform the method and/or apparatus and/or system disclosed herein.

Through the use of a computer or other digital technology, segmentation of anatomical regions and/or lesions from medical images may be performed with greater accuracy, speed, and reliability that relying on a human expert. Therefore, a greater number of medical images may be reviewed at one time thereby reducing backlogs for experts and further reducing errors made when the medical images themselves are actually reviewed.

BRIEF DESCRIPTION OF DRAWINGS

Embodiments will now be described, by way of example only and with reference to the accompanying drawings having like-reference numerals, in which.

SPECIFIC DESCRIPTION

Figure 1:
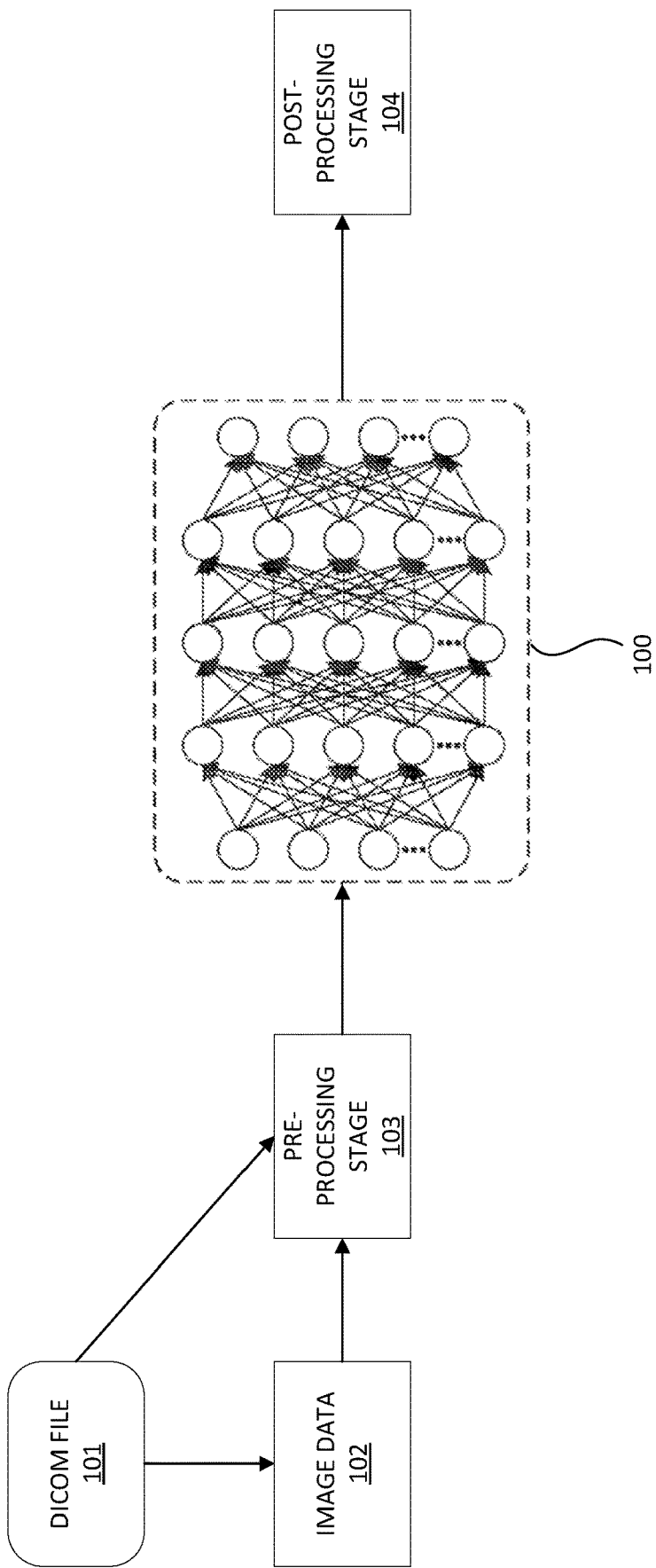
FIG. 1 shows a process of automated segmentation of anatomical regions.
Figure 2:
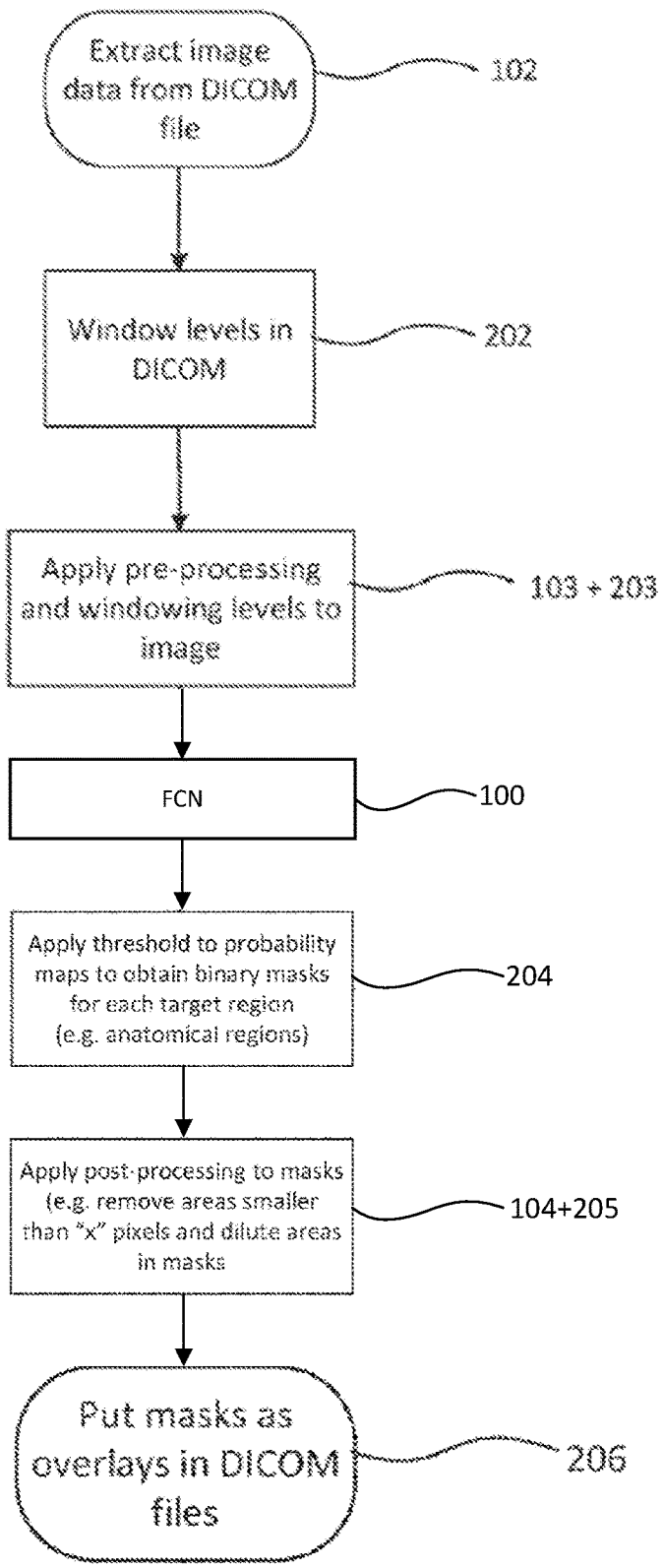
FIG. 2 shows a more detailed view of the process of automated segmentation of anatomical regions.
Figure 3:
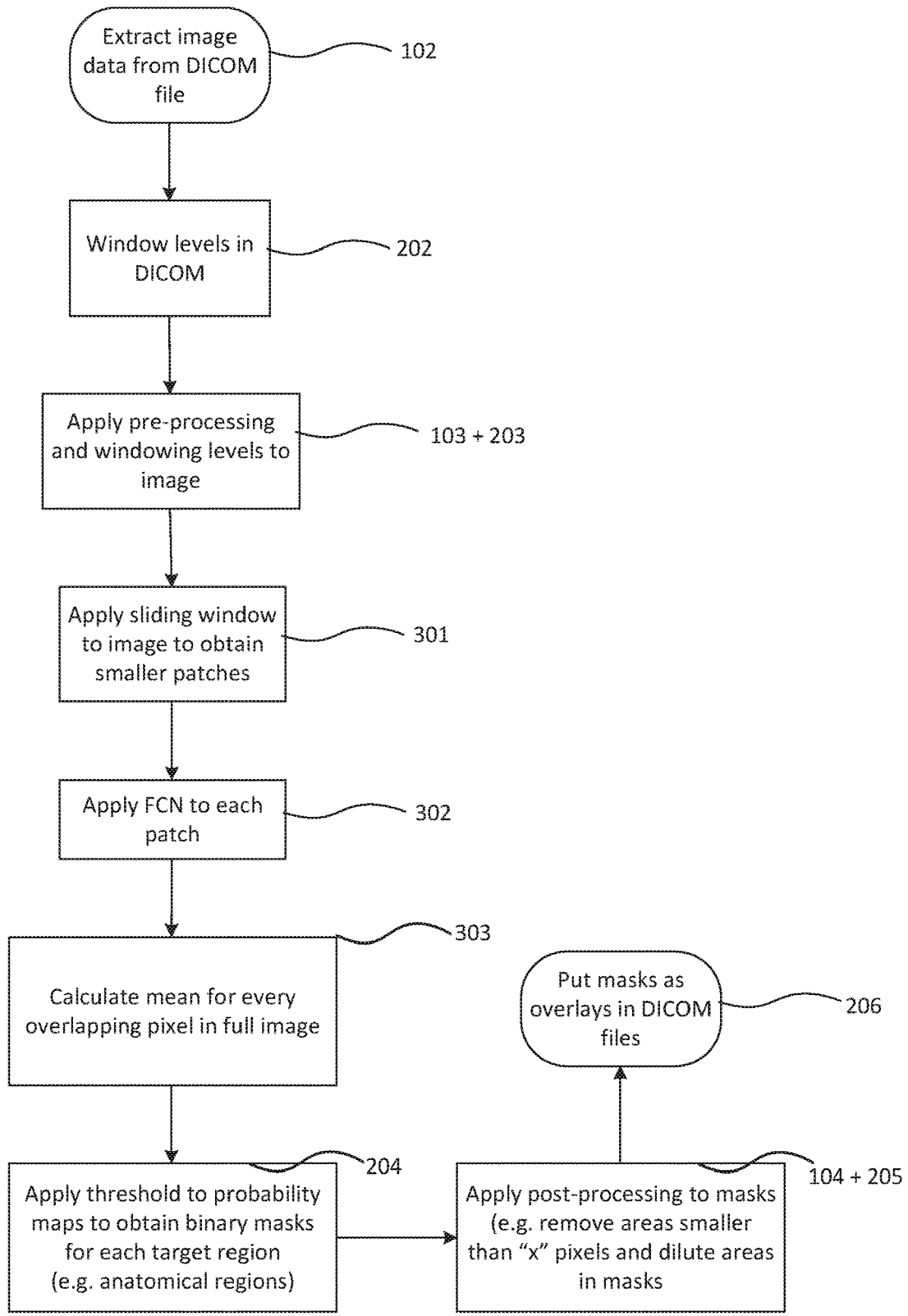
FIG. 3 shows a process of automated segmentation of lesion regions.
Figure 4:
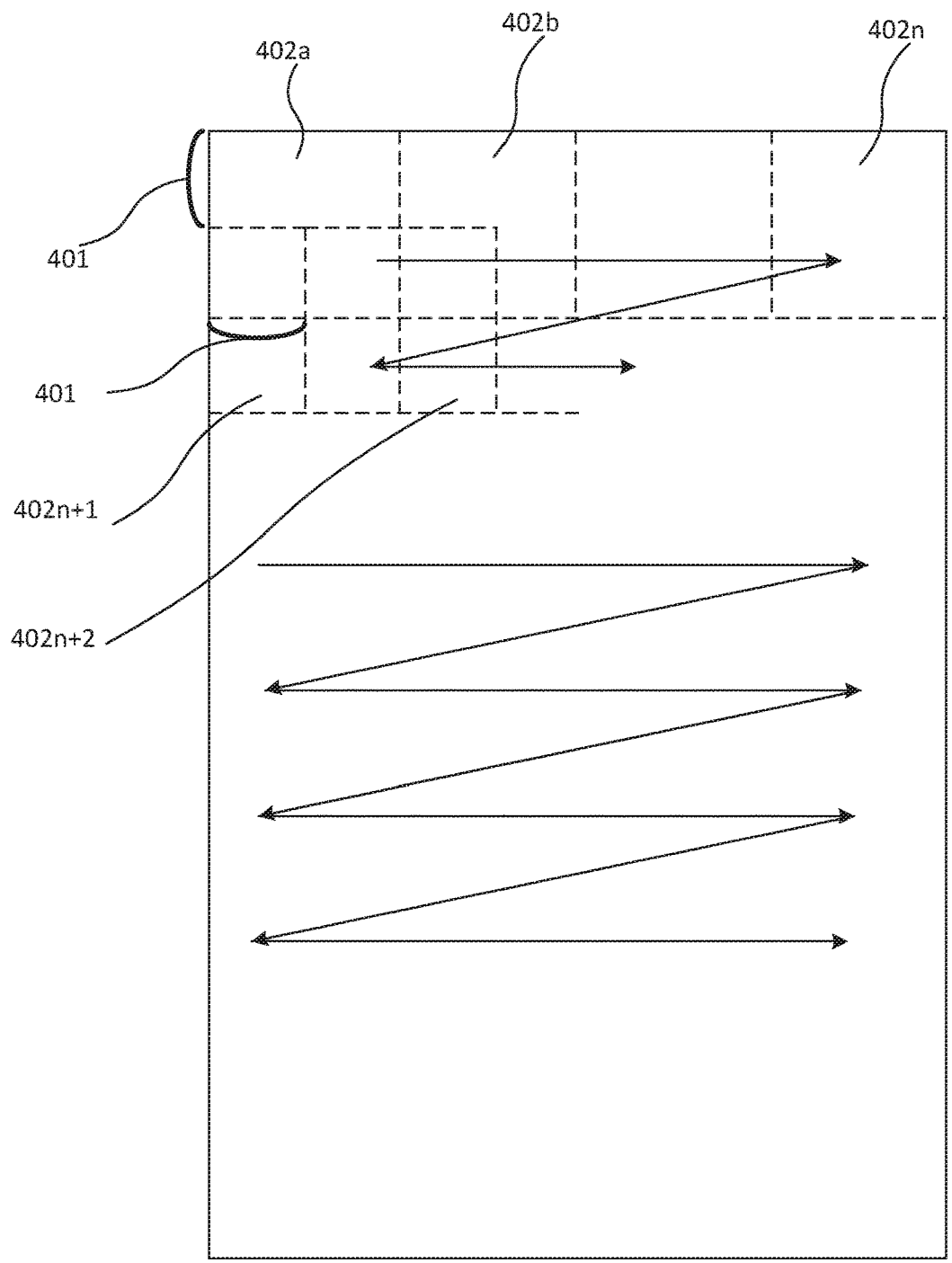
FIG. 4 shows a more detailed view of a sliding window arrangement.

Referring to FIGS. 1 to 4, a first embodiment will now be described. In this embodiment, a Digital Imaging and Communications in Medicine (DICOM) file 101 is provided as input data. DICOM is a conventional standard for transmitting and storing medical images, for example a mammogram. Image data 102 is then extracted from the DICOM file and an image is generated.

The image then undergoes a pre-processing stage 103. The image is loaded onto a 4D tensor of size [1, width, height, 1]. The pre-processing stage may comprise windowing the image data 203 to a predetermined windowing level 202. The windowing level defines the range of bit values considered in the image. Medical images are conventionally 16-bit images, wherein each pixel is represented as a 16-bit integer ranging from 0 to $2^{16}-1$, i.e. [0, 1, 2, . . . , 65535]. The information content is very high in these images, and generally comprises more information than what the human eye is capable of detecting. A set value for the windowing level is typically included within the DICOM file 202.

In some cases, it can be important to maintain image resolution. In this embodiment conventional graphics processing unit (GPU) constraints require that the image is divided into a plurality of patches in order to maintain resolution. Each patch is then provided to a Fully Convolutional Network (FCN). The larger the patch, the more context that can be provided but some precision may be lost. For example, in the case of a large image comprising a small tumour, if the FCN is instructed that somewhere in this patch there is a tumour, the network would need to learn how to find it first before it can be classified. In this embodiment patch sizes of 300×300 pixels are used, although larger and smaller patch sizes may be used.

In order to ensure that a prediction for each patch corresponds to a final output probability mask based on mean values for each pixel, a sliding window arrangement 301 is used. In order to use this arrangement, models may be trained on smaller patches sampled from an image. At "prediction/test time", i.e. after the model has been trained, a prediction is required for every pixel of the image, but the input to the model can only be a smaller patch owing to conventional hardware constraints. Therefore, the full image can be divided up into smaller patches and fed individually into the FCN 302. The model "slides" over the full images in a sliding window fashion and outputs a prediction for each patch. The outputs are then stitched together to generate an output map. Therefore, once training is complete, at prediction time the full image is divided into patches in the same sliding window fashion. For example, if each patch 402a is 100×100 pixels every time we slide, we move the patch with a specific number of pixels to the side ("the stride" 401). In the example shown in FIG. 4, this is half the patch, i.e. 50 pixels. The second patch 402b may comprise some overlap with a previous patch. Each patch is classified and that probability is given to every pixel within the patch. For example, if the probability of a patch being cancerous is 0.9, then every pixel in that patch is labelled as 0.9. If there is overlap, the mean of the number of overlapping pixels is calculated, although other arithmetic and/or mathematical operators may be used 303.

The image is then rescaled to a width of 800 pixels and a height of 800 pixels before it is provided to a Fully Convolutional Network (FCN) 100. The image can be rescaled to a larger or smaller size, or even not rescaled at all. The rescaled image is then supplied to the FCN 100. The FCN 100 is a type of network architecture that may be used for semantic segmentation tasks. Semantic segmentation is the task where a class is assigned to each pixel in an image. In this embodiment, the FCN 100 is a convolutional neural network without any fully connected layers. A fully connected layer can be expressed as a convolutional layer with 1×1 kernels. The network can be applied to an arbitrarily sized image (subject to hardware constraints). A conventional convolutional neural network (CNN) with fully connect layers only works on a specific image size. Hence, an FCN is a function mapping:

$$f: X \rightarrow Y$$

where X is a tensor of size [Batch size×Width×Height× #channels] with each element being in the set {0, . . . , $2^{16}-1$}. Y has the shape [Batch size×Width×Height× #classes], each element is between 0 and 1.

The FCN 100 may comprise any combination of one or more convolutional, hidden representation, activation, and/ or pooling layers. The activation layer in this embodiment is in the form of a sigmoid activation layer. In this embodiment the input is an image of 800×800 pixels, and the FCN 100 is operable to produce an output comprising a probability mask of 800×800 pixels, where each pixel represents a probability of belonging to a class. In a further embodiment, the same FCN 100 may be applied to an image of size 900×900 pixels, and hence produce an output probability mask of 900×900 pixels. A different probability mask may be generated for each of a plurality of anatomical regions. The FCN 100 is trained to generate such a probability mask by providing a set of input values and associated weights. During training, a correct class for each value is known, and hence it is possible to compare the FCN 100's calculated output probability mask to the correct values. An error term for each node in the FCN 100 can then be established, and the weights adjusted, so that for future input values the output probability mask is closer to the correct value.

The or each probability mask is then converted to one or more binary masks during a post-processing stage 104. The conversion from a probability mask to binary mask may be through thresholding the probabilities 204 which obtains a binary mask for each target region (for example, anatomical regions). Small areas in the binary mask may be removed 205. If the area (which may be represented by an identified number of pixels) is smaller than a specific predetermined threshold, then the area may be removed from the binary mask entirely. Similarly, holes in the segmentation itself may be removed. If a segmentation has an area of zeros, entirely surrounded by ones, then the zeros may be set to ones according to a predetermined threshold value for the area.

The binary mask is upscaled to the original size of the input image and stored in the DICOM file as an overlay 206. The overlay may comprise any markings one or more parts of the original image, for example by outlining different areas of human breast tissue. Typically, anatomical regions identified through the use of this method may comprise the pectoral muscle, the parenchyma, and/or the mammilla.

The generation of the binary mask is an entirely automated process, and requires no human action other than the input of a data to be analysed. Conventional segmentation methods rely on an expert, usually a radiologist, providing a seed region or starting point. Conversely, the method disclosed herein is operable to segment a region without any prior input other than an image.

Although the embodiments described with reference to FIGS. 1 to 4 may be used to segment anatomical regions and lesions, in a further embodiment the method may also be used to segment lesions. The lesions which may be segmented may comprise one or more cancerous growths, masses, abscesses, lacerations, calcifications, and/or other irregularities within biological tissue. In order for the FCN 100 to be optimised to perform such segmentation it may be trained using a different, more relevant, dataset. In practice, the network architecture for segmenting lesions may be in the form of a different embodiment. For example, a lesion segmentation tool for mammograms may comprise multiple paths, one of which is operable to analyse a higher-resolution medical image and a different path operable to analyse a lower-resolution image.

Mammography is a medical imaging modality widely used for breast cancer detection. Mammography makes use of "soft" X-rays to produce detailed images of the internal structure of the human breast—these images are called mammograms and this method is considered to be the gold standard in early detection of breast abnormalities which provide a valid diagnosis of a cancer in a curable phase.

Unfortunately, the procedure of analysing mammograms is often challenging. The density and tissue type of the breasts are highly varied and in turn present a high variety of visual features due to patient genetics. These background visual patterns can obscure the often tiny signs of malignancies which may then be easily overlooked by the human eye. Thus, the analyses of mammograms often leads to false-positive or false-negative diagnostic results which may cause missed treatment (in the case of false negatives) as well as unwanted psychological and sub-optimal downstream diagnostic and treatment consequences (in the case of false positives).

Most developed countries maintain a population-wide screening program, comprising a comprehensive system for calling in women of a certain age group (even if free of symptoms) to have regular breast screening. These screening programs require highly standardized protocols to be followed by experienced specialist trained doctors who can reliably analyse a large number of mammograms routinely. Most professional guidelines strongly suggest reading of each mammogram by two equally expert radiologists (also referred to as double-reading). Nowadays, when the number of available radiologists is insufficient and decreasing, the double-reading requirement is often impractical or impossible.

When analysing mammograms, the reliable identification of anatomical structures is important for visual evaluation and especially for analytic assessment of visual features based on their anatomic location and their relation to anatomic structures, which may have profound implications on the final diagnostic results. In the case that anatomic structures appear distorted they may also indicate the presence of possible malignancies.

Conventional X-ray is a medical imaging modality widely used for the detection of structural abnormalities related to the air containing structures and bones, as well as those diseases which have an impact on them. Conventional X-ray is the most widely used imaging method and makes use of "hard" X-rays to produce detailed images of the internal structure of the lungs and the skeleton. These images are called roentgenograms or simply X-rays.

Unfortunately, the procedure of analysing X-rays is often challenging, especially when analysing lung X-rays in order to detect infectious disease (e.g. TB) or lung cancer in early stage.

Most developed countries maintain a population-wide screening program, comprising a comprehensive system for calling in the population of a certain age group (even if free of symptoms) to have regular chest X-ray screening. These screening programs require highly standardized protocols to be followed by experienced specialist trained doctors who can reliably analyse a large number of X-rays routinely.

When analysing X-ray images, the reliable identification of anatomical structures is important for visual evaluation and especially for analytic assessment of visual features based on their anatomic location and their relation to anatomic structures, which may have profound implications on the final diagnostic results. In the case that anatomic structures appear distorted they may also indicate the presence of possible malignancies.

Cross-sectional medical imaging modalities are widely used for detection of structural or functional abnormalities and diseases which have a visually identifiable structural impact on the human internal organs. Generally, the images demonstrate the internal structures in multiple cross-sections of the body. The essence of the most widely used cross-sectional techniques are described below.

Computed tomography (CT) is a widely used imaging method and makes use of "hard" X-rays produced and detected by a specially rotating instrument and the resulted attenuation data (also referred to as raw data) are presented by a computed analytic software producing detailed images of the internal structure of the internal organs. The produced sets of images are called CT-scans which may constitute multiple series with different settings and different contrast agent phases to present the internal anatomical structures in cross sections perpendicular to the axis of the human body (or synthesized sections in other angles).

Magnetic Resonance Imaging (MRI) is an advanced diagnostic technique which makes use of the effect magnetic field impacts on movements of protons which are the utmost tiniest essential elements of every living tissue. In MRI machines the detectors are antennas and the signals are analysed by a computer creating detailed images if the internal structures in any section of the human body. MRI can add useful functional information based on signal intensity of generated by the moving protons.

However, the procedure of analysing any kind of cross-sectional images is often challenging, especially in the case of oncologic disease as the initial signs are often hidden and appearance of the affected areas are only minimally differed from the normal.

When analysing cross sectional scans, diagnosis is based on visual evaluation of anatomical structures. The reliable assessment, especially for analytic assessment, of visual appearance based on their anatomic location and their relation to anatomic structures, may have profound implications on final diagnostic results. In the case that anatomic structures appear distorted they may also indicate the presence of possible malignancies.

Generally, in the case of all diagnostic radiology methods (which include mammography, conventional X-ray, CT, MRI), the identification, localisation (registration), segmentation and classification of abnormalities and/or findings are important interlinked steps in the diagnostic workflow.

In the case of ordinary diagnostic workflows carried out by human radiologists, these steps may only be partially or sub-consciously performed but in the case of computer-based or computer-aided diagnoses and analyses the steps often need to be performed in a clear, concrete, descriptive and accurate manner.

Locality and classification may define and significantly influence diagnoses. Both locality and classification may be informed by segmentation in terms of the exact shape and extent of visual features (i.e. size and location of boundaries, distance from and relation to other features and/or anatomy). Segmentation may also provide important information regarding the change in status of disease (e.g. progression or recession).

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

Any system feature as described herein may also be provided as a method feature, and vice versa. As used herein, means plus function features may be expressed alternatively in terms of their corresponding structure.

Any feature in one aspect of the invention may be applied to other aspects of the invention, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention claimed is:

1. A computer-aided method of segmenting regions in medical images, the method comprising:
  receiving input data;
  analysing the input data by identifying one or more
    regions, wherein analysing the input data is performed using one or more Fully Convolutional Networks (FCNs), wherein the one or more FCNs do not have any dense layers, wherein each neuron of a dense layer receives input from each neuron of a previous layer;

determining one or more characteristics for the one or more regions in the input data; and generating output segmentation data in dependence upon the characteristics for the one or more regions.

2. The method of claim 1, wherein the or each FCN comprises one or more convolutional layers and/or one or more hidden representations.

3. The method of claim 1, wherein the or each FCN comprises one or more hidden representations.

4. The method of claim 1, wherein the or each FCN comprises one or more activation layers, the one or more activation layers comprising one or more rectified linear units (ReLU) and/or exponential linear units (ELU).

5. The method of claim 1, wherein the or each FCN comprises one or more sigmoid activation layers and/or softmax functions for the or each region.

6. The method of claim 1, wherein the input data comprises medical image data and/or one or more Digital Imaging and Communications in Medicine (DICOM) files.

7. The method of claim 6, wherein the medical image data comprises one or more mammograms, the one or more regions comprises an anatomical region, and the anatomical region comprise at least part of a human breast area.

8. The method of claim 6, wherein the medical image data comprises a 4D tensor.

9. The method of claim 8, wherein: the 4D tensor is of size [1, height, width, 1].

10. The method of claim 9, wherein pixel values of the medical image data are fit to a windowing level supplied by the DICOM file and then represented as 16-bit, and wherein the medical image data is rescaled to a width of between 750 and 900 pixels and/or a height of between 750 and 900 pixels.

11. The method of claim 1, wherein the output segmentation data comprises an overlay.

12. The method of claim 11, wherein the overlay comprises a segmentation outline and/or probability map showing one or more locations of the one or more regions.

13. The method of claim 12, wherein voids within the segmentation outline are operable to be removed.

14. The method of claim 1, further comprising one or more of:

generating one or more probability masks for the one or more regions;

converting one or more of the one or more probability masks to one or more binary masks, wherein the converting is performed by thresholding the probabilities; and removing one or more parts of the one or more binary masks with reference to an assigned threshold.

15. The method of claim 14, wherein the one or more binary masks are one or both of: upscaled to the original size of the input data; and/or stored in the form of a DICOM file.

16. The method of claim 14, wherein the one or more binary masks comprise one or more identifications of masses and/or calcifications, and the one or more regions comprises an anatomical region and/or a lesion.

17. The method of claim 1, wherein the input data comprises a plurality of patches and analysing the input data comprises:

analysing the plurality of patches of the input data through sliding windows;

calculating a prediction score for each of the plurality of patches; and determining an overall prediction score comprising a mean score across the plurality of patches.

18. The method of claim 17, wherein calculating the prediction score comprises:

determining a probability that a given patch is cancerous; and applying the determined probability to each pixel within the given patch.

19. A system for segmenting regions in medical images, the system comprising:

a memory including instructions;

one or more processors to execute the instructions to receive input data;

analyse the input data by identifying one or more regions, wherein analysing the input data is performed using one or more Fully Convolutional Networks (FCNs), wherein the one or more FCNs do not have any dense layers, wherein each neuron of a dense layer receives input from each neuron of a previous layer;

determine one or more characteristics for the one or more regions in the input data; and generate output segmentation data in dependence upon the characteristics for the one or more regions.

20. A computer program product including one or more non-transitory machine readable mediums encoded with instructions that when executed by one or more processors cause a process to be carried out for segmenting regions in medical images, the process comprising:

receiving input data;

analysing the input data by identifying one or more regions, wherein analysing the input data is performed using one or more Fully Convolutional Networks (FCNs), wherein the one or more FCNs do not have any dense layers, wherein each neuron of a dense layer receives input from each neuron of a previous layer;

determining one or more characteristics for the one or more regions in the input data; and generating output segmentation data in dependence upon the characteristics for the one or more regions.

* * * * *